United States Patent [19]

Mallart et al.

[11] Patent Number: 5,543,526
[45] Date of Patent: Aug. 6, 1996

[54] 1-AMINO-4-(1H-IMIDAZOLE)-AMINOBUTANEBORONIC ACID DERIVATIVES, THEIR PREPARATION AND USE AS SYNTHETIC INTERMEDIATES

[75] Inventors: Sergio Mallart, Orsay; Gilbert Lassalle, Clamart; Thomas Andrew Purcell, Montfort l'Amaury; Jean Claude Muller, Morsang sur Orge, all of France

[73] Assignee: Synthelabo, Le Plessis Robinson, France

[21] Appl. No.: 419,923

[22] Filed: Apr. 11, 1995

[30] Foreign Application Priority Data

Apr. 12, 1994 [FR] France .................. 94.04287

[51] Int. Cl.⁶ .................. C07F 5/04; C10M 1/10; C10M 1/54
[52] U.S. Cl. .................. 548/110; 558/288
[58] Field of Search .................. 548/110

[56] References Cited

U.S. PATENT DOCUMENTS

| | | | |
|---|---|---|---|
| 4,298,486 | 11/1981 | Horodysky et al. | 548/110 X |
| 4,554,086 | 11/1985 | Karol et al. | 548/110 X |
| 4,963,655 | 10/1990 | Kinder et al. | 530/331 |
| 5,187,157 | 2/1993 | Kettner et al. | 514/018 |

FOREIGN PATENT DOCUMENTS

| | | | |
|---|---|---|---|
| 0157969 | 10/1985 | European Pat. Off. | 548/110 |
| 5-239069 | 9/1993 | Japan | 548/110 |

*Primary Examiner*—Floyd D. Higel
*Attorney, Agent, or Firm*—Jacobson, Price, Holman & Stern, PLLC

[57] ABSTRACT

A compound of formula (I)

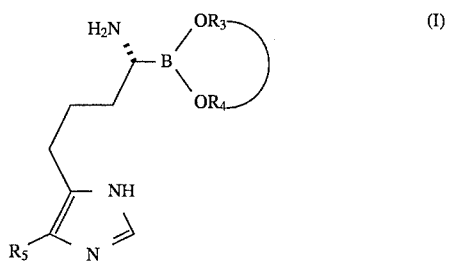

in which

R₃ and R₄ together represent the residue of a dihydroxy compound, and

R₅ represents a hydrogen atom or a $(C_1-C_4)$ alkyl group, or a salt thereof, and its use as a synthetic intermediate.

10 Claims, No Drawings

1-AMINO-4-(1H-IMIDAZOLE)-AMINOBUTANEBORONIC ACID DERIVATIVES, THEIR PREPARATION AND USE AS SYNTHETIC INTERMEDIATES

The subject of the present invention is aminoboronic acid derivatives, their preparation and their use as synthetic intermediates.

The present invention provides a compound of formula (I)

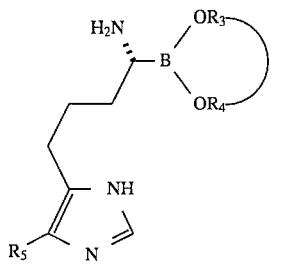

in which
R₃ and R₄ together represent the residue of a dihydroxy compound, and
R₅ represents a hydrogen atom or a $(C_1-C_4)$alkyl group, or a salt thereof.

Preferred are compounds or salts thereof in which $R^3$ and $R^4$ together represent the residue of 2,3-butanediol, 2,3-dimethyl-2,3-butanediol or (1α,3α,5α)-2,6,6-trimethylbicyclo[3.1.1]heptane-2,3-diol [(+)-α-pinanediol].

The compounds of the invention can exist in the form of optical or geometric isomers which are pure or in the form of mixtures. They can exist in the form of free bases or of salts, for example, with hydrogen chloride.

The compounds of the invention can be synthesized according to Scheme 1. [3aS-(3aα,4β,6β,7aα)]-2-(3-bromopropyl)-3a,5,5-trimethylhexahydro-4,6-methano-1,3,2-benzodioxaborole of formula (IV) is reacted with sodium iodide in a solvent such as, for example, acetone in order to obtain [3aS-(3aα, 4β,6β,7aα)]-2-(3-iodopropyl)-3a,5,5

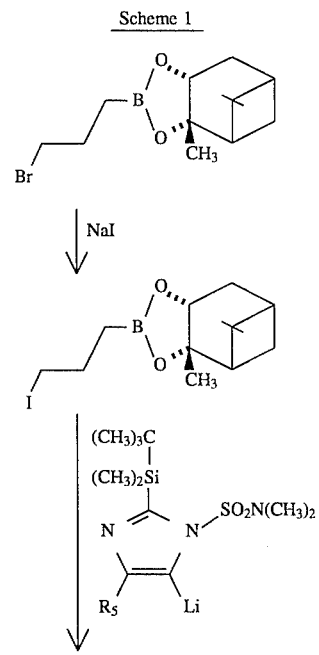

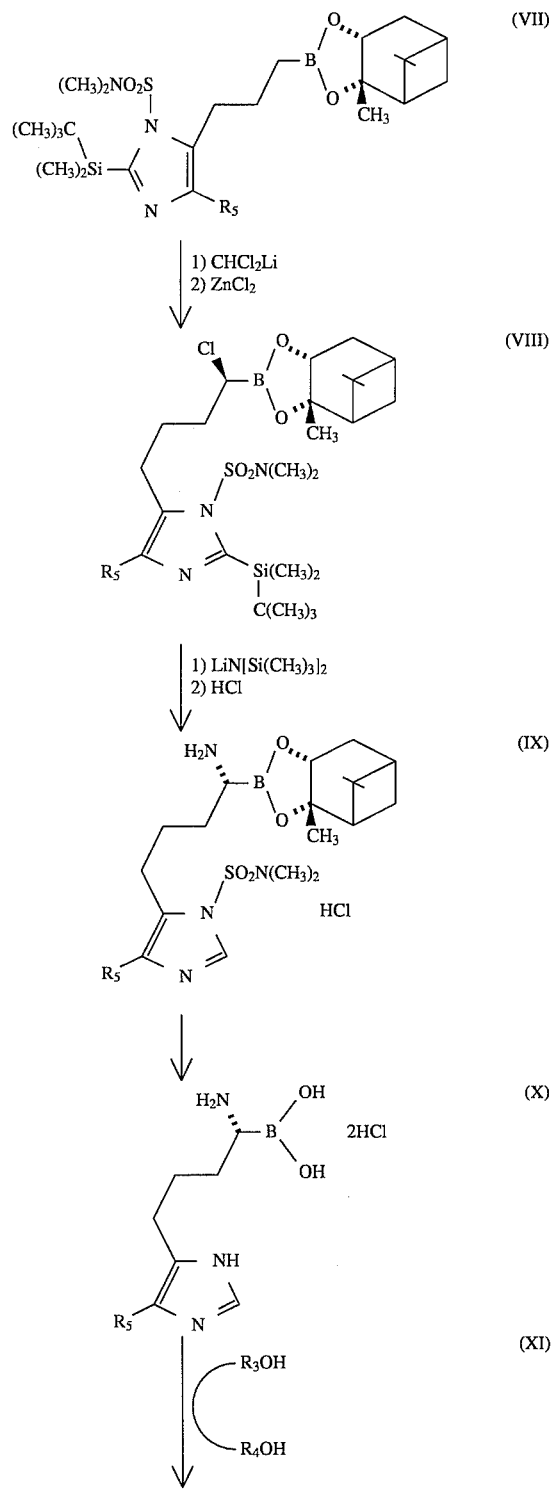

-continued
Scheme 1

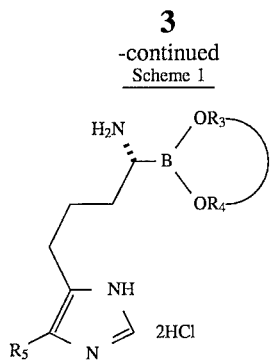

(I)

-trimethylhexahydro-4,6-methano-1,3,2-benzodioxaborole of formula (V) which is condensed with a compound of formula (VI) (in which $R_5$ represents a hydrogen atom or a $(C_1-C_4)$alkyl group) in order to obtain the compound of formula (VII); the reaction is carried out in a solvent such as tetrahydrofuran, at a temperature of between −78° and +20° C. Then, according to a process analogous to that described by Mattheson, Organometallics, (1984), 3, 614, the compound of formula (VII) is reacted with dichloromethyllithium, in the presence of zinc chloride, in a solvent such as tetrahydrofuran, at a temperature of between −100° and +20° C., in order to obtain the compound of formula (VIII) which is reacted with lithium bis(trimethylsilyl)amide; the reaction is carried out in a solvent such as tetrahydrofuran at a temperature of between −78° and +20° C. The compound thus obtained is then treated with hydrochloric acid in a solvent such as, for example, dioxane and the hydrochloride of formula (IX) is obtained which is hydrolyzed in order to form the dihydrochloride of the (R)-α-aminobutaneboronic acid of formula (X) and the acid thus obtained is then reacted with a diol of formula (XI) in which $R_3$ and $R_4$ together represent the residue of a dihydroxy compound.

The starting compounds are commercially available or are described in the literature or can be prepared according to methods which are described therein or which are known to those skilled in the art.

Thus, [3aS-(3aα,4β,6β,7aα)]-2-(3-bromopropyl)-3a,5,5-trimethylhexahydro-4,6-methano-1,3,2-benzodioxaborole is described in European Patent No. 0,293,881. 2-[(1,1-Dimethylethyl)dimethylsilyl]-N,N-dimethyl-1H-imidazole-1-sulphonamide is described by Ngochindo in J. Chem. Soc. Perkin Trans. (1990), 1, 1645 and 2-[1,1 -dimethylethyl)dimethylsilyl]-N,N,4-trimethyl-1H-imidazole-1-sulphonamide is prepared by an analogous method.

The present invention also provides a process for the production of a compound or a salt thereof of the present invention which process comprises hydrolyzing the free base of a compound of formula (IX) as hereinbefore defined or a salt thereof in order to obtain the free base of a compound of formula (X) as hereinbefore described or a salt thereof which is reacted with a diol to obtain a compound of formula (I) or a salt thereof and, where appropriate optionally converting it into the free base or a salt thereof.

The following Examples illustrate the preparation of several compounds in accordance with the invention. The elemental microanalyses and the IR and NMR spectra confirm the structure of the compounds obtained.

EXAMPLE 1

[3aS-[2(R),3aα,4β,6β,7aα]]-α-(3a,5,5-Trimethylhexahydro-4,6-methano-1,3,2-benzodioxaborol-2-yl)-1H-imidazole-4(5)-butanamine Hydrochloride (1:2)

1.1 [3aS-(3aα,4β,6β,7aα)]-2-(3-Iodopropyl)-3a,5,5-trimethylhexahydro-4,6-methano-1,3,2-benzodioxaborole A solution of 37 g (122 mmol) of [3aS-( 3aα,4β,6β,7aα)]-2-(3-bromopropyl)-3a,5,5-trimethylhexahydro-4,6-methano-1,3,2-benzodioxaborole and 72.7 g (488 mmol) of sodium iodide in 500 ml of acetone is brought to the reflux temperature for 24 hours. The solvent is evaporated and the residue is taken up in a mixture of 500 ml of ether and 100 ml of water containing 1 g of sodium sulphite. The organic phase is dried over magnesium sulphate, filtered and evaporated. 40 g of product are obtained, which product is used directly in the following stage.

Yield=95%

1.2. [3aS-(3aα,4β,6β,7aα)]-2-[(1,1-Dimethylethyl)dimethylsilyl]-N,N-dimethyl-4(5)-[3-(3a,5,5-trimethylhexahydro-4,6-methano-1,3,2-benzodioxaborol-2-yl)propyl]-1H-imidazole-1-sulphonamide 70.5 g (244 mmol) of 2-[1,1-dimethylethyl)dimethylsilyl]-N,N-dimethyl-1H-imidazole-1-sulphonamide are dissolved in 250 ml of tetrahydrofuran. The reaction mixture is cooled to −78° C. and 152 ml (244 mmol) of a 1.6M solution of n-butyllithium in hexane are added. The reaction mixture is left stirring for 1 hour at −78° C. and then 40 g (115 mmol) of [3aS-(3aα,4β,6β,7aα)]-2-(3-iodopropyl)- 3a,5,5-trimethylhexahydro-4,6-methano-1,3,2-benzodioxaborole, in solution in 100 ml of tetrahydrofuran, are added. The reaction mixture is stirred between −78° C. and +20° C. for 1 hour and then at 20° C. for 2 hours. The reaction mixture is poured onto 350 ml of an ice/water mixture containing 14.5 g (121 mmol) of sodium hydrogensulphate. The aqueous phase is extracted with 3 times 100 ml of ether and the ethereal phases are combined, dried over magnesium sulphate, filtered and evaporated. The residue is purified by chromatography on a column of silica gel, elution being carried out with a 20% solution of ethyl acetate in hexane. 45 g of product are obtained.

Yield=73%. $[\alpha]_D^{20}$=+12.5° (c=1.9, chloroform).

1.3. [3aS-[2(S),3aα,4β,6β,7aα]]-4(5)-[4-Chloro-4-(3a,5,5-trimethylhexahydro-4,6-methano-1,3,2-benzodioxaborol-2-yl)butyl]-2-[(1,1-dimethylethyl)dimethylsilyl]-N,N,-dimethyl-1H-imidazole-1-sulphonamide A solution of 8.3 g (98 mmol) of dichloromethane in 100 ml of tetrahydrofuran is cooled to −100° C. 39.1 ml (98 mmol) of a 2.5M solution of n-butyllithium in hexane are added. The reaction mixture is left for 15 minutes at this temperature and then 45 g (89 mmol) of [3aS-(3aα,4β,6β, 7aα)]-2 -[(1,1-dimethylethyl)dimethylsilyl]-N,N-dimethyl-4(5)-[3 -(3a,5,5-trimethylhexahydro-4,6-methano-1,3,2-benzodioxaborol-2 -yl)propyl]-1H-imidazole-1-sulphonamide, in solution in 50 ml of tetrahydrofuran, are added. The reaction mixture is left for 15 minutes at −100° C. and 9.8 g (70 mmol) of a solution of zinc chloride in 50 ml of tetrahydrofuran are added. The reaction mixture is left to return to +20° C. over 16 hours. Evaporation is carried out under vacuum and the residue is taken up in a mixture of 200 ml of dichloromethane and 50 ml of water. The phases are separated and the aqueous phase is extracted with 100 ml of dichloromethane. The organic phases are combined, dried over magnesium sulphate, filtered and evaporated. The coloured residue obtained is purified by chromatography on a column of silica gel, elution being carried out with an ethyl acetate/hexane (20/80) mixture. 40 g of product are obtained in the form of a colourless oil.

Yield=80%. $[\alpha]_D^{20}$=+15.9° (c=2.65, chloroform).

1.4. [3aS-[2(R),3aα,4β,6β,7aα]]-4(5)-[4-Amino-4-(3a, 5,5-trimethylhexahydro-4,6-methano-1,3,2-benzodioxaborol-2-yl)butyl]-N,N-dimethyl-1H-imidazole-1-sulphonamide hydrochloride (1:1)

12.6 g (78 mmol) of 1,1,1,3,3,3-hexamethyldisilazane are dissolved in 80 ml of tetrahydrofuran and 31 ml (78 mmol) of a 2.5M solution of n-butyllithium in hexane are added. The reaction mixture is left for 1 hour at −78° C. and 40 g (71 mmol) of [3aS-[2(S),3aα,4β,6β,7aα]]-4(5)-[4-chloro-4-(3a, 5,5-trimethylhexahydro-4,6-methano-1,3,2-benzodioxaborol-2 -yl)butyl]-2-[(1,1-dimethylethyl)dimethylsilyl]-N,N-dimethyl-1 H-imidazole-1-sulphonamide, in solution in 80 ml of tetrahydrofuran, are added. The reaction mixture is left stirring for 1 hour at −78° C. and for 16 hours at +20° C. The reaction mixture is cooled to −78° C., 78 ml (312 mmol) of a 4N solution of hydrochloric acid in dioxane are added and the reaction mixture is left stirring for 1 hour at −78° C. and for 2 hours at +20° C. Evaporation is carried out under vacuum and the residue is taken up in 200 ml of chloroform. Filtration and evaporation are carried out. 32 g of product are obtained in the form of an oil which is triturated in ether. The product is obtained in the form of a solid.

Yield=89% Melting point=90°–92° C. $[\alpha]_D^{20}$=+11° (c=1, methanol).

1.5. [3aS-[2(R),3aα,4β,6β,7aα]]-α-(3a,5,5-Trimethylhexahydro-4,6-methano-1,3,2-benzodioxaborol-2-yl)-1H-imidazole-4(5)-butanamine Hydrochloride (1:2)

32 g (70 mmol) of [3aS-[2(R),3aα,4β,6β,7aα]]-4(5)-[4-amino-4-(3a,5,5-trimethylhexahydro-4,6methano-1,3,2-benzodioxaborol-2-yl)butyl]-N,N-dimethyl-1H-imidazole-1-sulphonamide hydrochloride, in solution in 200 ml of 4N hydrochloric acid, are brought to reflux for 3 hours. The solution is extracted with 4 times 100 ml of ether and evaporation is carried out to dryness. The residue is taken up in 100 ml of methanol and 11.9 g (70 mmol) of [1R-(1α,2α,3α,5α)]-2,6,6-trimethylbicyclo[3.1.1]heptane-2,3-diol are added. The reaction mixture is left stirring for 16 hours at 20° C. and evaporated to dryness. 27 g of product are obtained in the form of an oil which is triturated in ether.

Melting point=75°–80° C.

EXAMPLE 2

[3aS-[2R,3aα,4β,6β,7aα]]-5-Methyl-α-(3a,5,5-trimethylhexahydro-4,6-methano-1,3,2-benzodioxaborol-2-yl)-1H-imidazole-4 -butanamine Hydrochloride (1:2)

It is prepared according to the method described in Example 1, from 2-[(1,1-dimethylethyl)dimethylsilyl]-N,N,4 -trimethyl-1H-imidazole-1-sulphonamide. The product is obtained in the form of a coloured solid.

Melting point=70°–75° C.

The compounds according to the invention are useful as intermediate in the synthesis of compounds of formula (1)

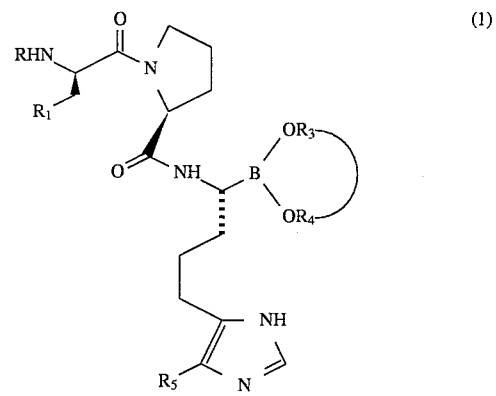

in which

R represents a hydrogen atom, a straight or branched ($C_1$–$C_4$)alkyl group, a —COR' group, where R' is a straight or branched chain ($C_1$–$C_4$)alkyl group, or a —$(CH_2)_n CO_2 R''$ group, where R" is a hydrogen atom, a straight or branched ($C_1$–$C_4$)alkyl group or a phenylmethyl group and n is from 0 to 2;

$R_1$ represents a phenyl group, a 1-naphthyl group, a 2-naphthyl group or a cyclohexyl group, $R_3$ and $R_4$ together represent the residue of a dihydroxylated compounds such as, for example, 2,3-butanediol, 2,3-dimethyl- 2,3-butanediol or (1α,3α,5α)-2,6,6-trimethylbicyclo[3.1.1]heptane-2,3-diol [(+)-α-pinanediol] and $R_5$ represents a hydrogen atom or a ($C_1$–$C_4$)alkyl group.

Compounds of formula (1) can be synthesized as shown in Scheme 2:

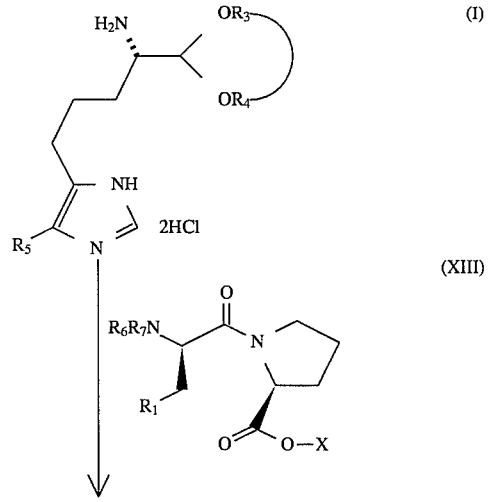

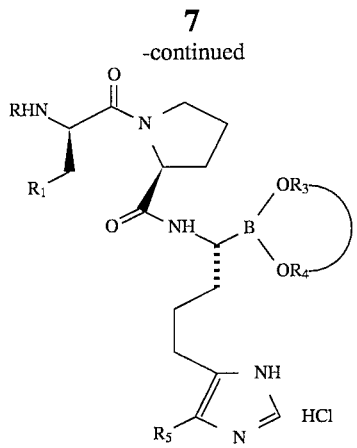

A compound of the present invention is coupled with an activated form of a dipeptide of formula (XIII) (in which $R_1$ is as defined above, $R_6$ represents either a hydrogen atom when $R_7$ represents a straight or branched —$CO(C_1-C_4)$ alkyl group, or a straight or branched —$CO_2(C_1-C_4)$ alkyl group when $R_7$ represents a hydrogen atom, or a straight or branched $(C_1-C_4)$ alkyl group and X represents either the pyrrolidin-1-yl-2,5-dione group or the 2-methylpropyloxycarbonyl group) to give a compound of formula (1) which is treated with hydrochloric acid to obtain the corresponding salt.

This process is discussed in more detail in French Publication No. 2718451.

Examples 3 and 4 which follow illustrate this synthesis.

EXAMPLE 3

[3aS-[2(R),3aα,4β,6β,7aα]]-N-Acetyl-D-phenylalanyl-N-[4-(1H-imidazol-4(5)-yl-1-(3a,5,5-trimethylhexahydro-4,6methano-1,3,2-benzodioxaborol-2-yl)butyl]-L-prolinamide Hydrochloride (1:1)

3.1. Ester of N-acetyl-D-phenylalanyl-L-proline with 1-hydroxypyrrolidine-2,5-dione 6 g (20 mmol) of N-acetyl-D-phenylalanyl-L-proline are suspended in a mixture of 100 ml of ethyl acetate and 5 ml of dimethylformamide. 2.53 g (22 mmol) of 1-hydroxypyrrolidine- 2,5-dione are added and the mixture is cooled to 0° C. 4.53 g (22 mmol) of 1,3-dicyclohexylcarbodiimide are then added, in small portions, in the solid form. The reaction mixture is stirred for 20 hours at 20° C. and the suspension is filtered. The filtrate is washed successively with 20 ml of a 5% sodium hydrogencarbonate solution and then with a saturated sodium chloride solution and dried over magnesium sulphate. The residue obtained is triturated in ether. 8 g of glassy product are obtained, which product is used as is in the following stage.

3.2 [3aS-[2(R),3aα,4β,6β,7aα]]-N-Acetyl-D-phenylalanyl-N-[4-(1H-imidazol-4(5)-yl)-1-(3a,5,5-trimethylhexahydro-4,6-methano-1,3,2-benzodioxaborol-2-yl)butyl]-L-prolinamide Hydrochloride (1:1)

2.4 g (6.2 mmol) of [3aS-[2(R),3aα,4β,6β,7aα]]-α-(3a,5,5-trimethylhexahydro-4,6-methano-1,3,2-benzodioxaborol-2-yl)-1H-imidazole-4(5)-butanamine hydrochloride are dissolved in 20 ml of dichloromethane, 2.5 g (6.4 mmol) of the ester of N-acetyl-D-phenylalanyl-L-proline with 1-hydroxypyrrolidine- 2,5-dione are added and the mixture is cooled to −30° C. 3.6 ml (25.6 mmol) of triethylamine are added dropwise and the mixture is stirred for 2 hours between −30° C. and +20° C. and then for 2 hours at +20° C. 20 ml of a 5% aqueous sodium hydrogencarbonate solution are then added and the aqueous phase is then extracted with 2 times 20 ml of dichloromethane. The organic phases are combined, dried over sodium sulphate, filtered and evaporated.

The residue is taken up in 10 ml of isopropanol and treated at 0° C. with 64 ml of a 0.1N solution of hydrochloric acid in isopropanol. After evaporation, the residue is decoloured with animal charcoal in ethyl acetate and purified on a Sephadex® LH-20 column, elution being carried out with methanol. Evaporation is carried out and the residue is triturated in ether. 2 g of product are obtained in the form of a colourless solid.

Melting point=130°–135° C. Yield=51% $[\alpha]_D^{20}$=−112.1° (c=1, chloroform).

EXAMPLE 4

1,1-Dimethylethyl [3aS-[2[R[S(R)]],3aα,4β,6β,7aα]]-[2-[2-[[[4-(5-methyl-1H-imidazol-4-yl)-1-(3a,5,5-trimethylhexahydro-4,6-methano-1,3,2-benzodioxaborol-2-yl)butyl]amino]carbonyl]pyrrolidin-1-yl]-2-oxo-1-(phenylmethyl)ethyl]carbamate Hydrochloride (1:1)

The method described in Example 3 is used, by condensing [3aS-[2R,3aα,4β,6β,7aα]]-5-methyl-α-(3a,5,5 -trimethylhexahydro-4,6-methano-1,3,2-benzodioxaborol-2-yl)-1H-imidazol-4 -butanamine hydrochloride with the ester of N-[(1,1 -dimethylethoxy)carbonyl]-D-phenylalanyl-2-proline with 1-hydroxypyrrolidine-2,5-dione. 600 mg of product are obtained.

Yield=28% M.p.=85°–90° C. $[\alpha]_D^{20}$=−53.2° (c=0.86, methanol).

We claim:

1. A compound of formula (I)

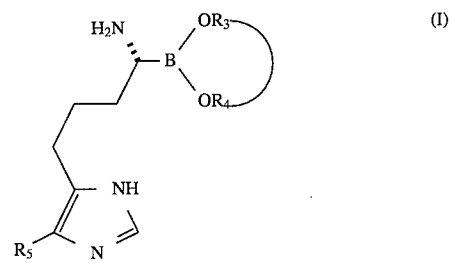

in which $R_3$ and $R_4$ together represent the residue of a dihydroxy compound, and $R_5$ represents a hydrogen atom or a $(C_1-C_4)$alkyl group, or a salt thereof.

2. A compound according to claim 1 or a salt thereof in which $R^3$ and $R^4$ together represent the residue of 2,3-butanediol, 2,3-dimethyl-2,3-butanediol or (1α,3α,5α)- 2,6,6-trimethylbicyclo[3.1.1]heptane-2,3-diol [(+)-α-pinanediol].

3. A compound according to claim 1 which is in the form of the hydrochloride salt.

4. A process for the production of a compound or a salt thereof as defined in claim 1, which process comprises hydrolysing a compound of formula (IX)

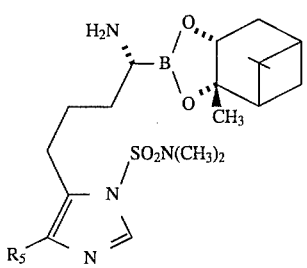 (IX)

or a salt thereof, in which $R_5$ is a hydrogen atom or a (C1-C$_4$)alkyl group, in order to obtain a compound of formula (X)

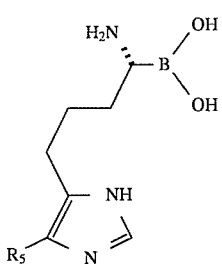 (X)

or a salt thereof, in which $R_5$ is as defined above, which is reacted with a diol to obtain a compound of formula (I) or a salt thereof.

5. A process according to claim 4 in which the compound of formula (VIII)

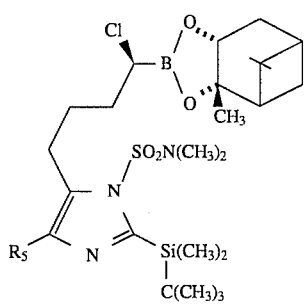 (VIII)

wherein $R_5$ is a hydrogen atom or a (C1-C$_4$)alkyl group, is reacted with lithium bis(trimethylsilyl)amide to form the compound of formula (IX).

6. A process according to claim 5 in which a compound of formula (VII)

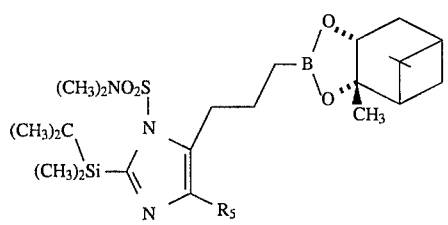 (VII)

wherein $R_5$ is a hydrogen atom or a (C1-C$_4$)alkyl group, is reacted with dichloromethyllithium, to obtain the compound of formula (VIII).

7. A process according to claim 6 in which a compound of formula (V)

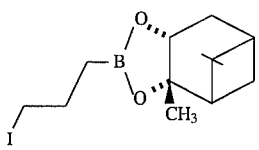 (V)

is condensed with a compound of formula (VI)

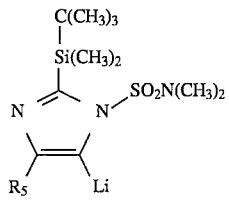 (VI)

wherein $R_5$ is a hydrogen atom or a (C1-C$_4$)alkyl group, to give the compound of formula (VII).

8. A process according to claim 7, in which a compound of formula (IV)

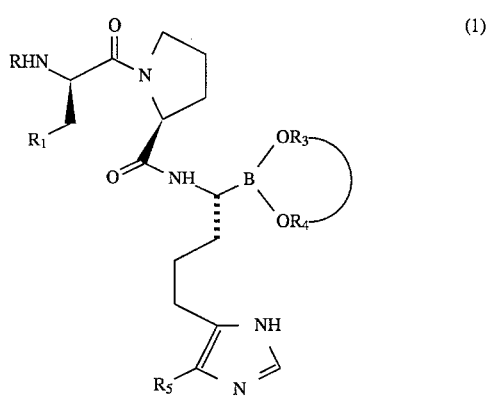 (IV)

is reacted with sodium iodide in an aprotic solvent, to give the compound of formula (V).

9. A process for synthesis of compounds of formula (1)

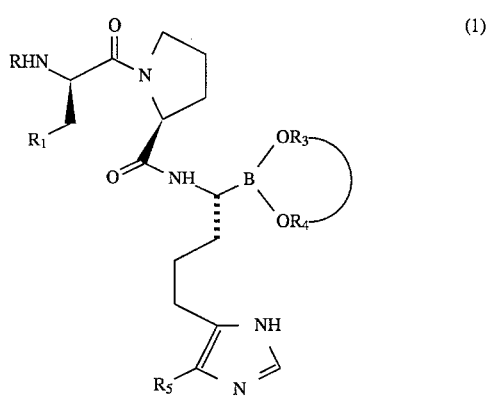 (1)

in which

R represents a hydrogen atom, a straight or branched (C$_1$–C$_4$)alkyl group, a —COR' group, where R' is a straight or branched (C$_1$–C$_4$)alkyl group, or a —(CH$_2$)$_n$CO$_2$R" group, where R" is a hydrogen atom, a straight or branched (C$_1$–C$_4$)alkyl group, or a phenylmethyl group, and n=0 to 2, $R_1$ represents a phenyl group, a 1-naphthyl group, a 2-naphthyl group, or a cyclohexyl group, $R_3$ and $R_4$ together represent the residue of a dihydroxylated compound and $R_5$ represents a hydrogen atom or a (C$_1$–C$_4$)alkyl group, comprising coupling a compound according to claim 1 with an activated form of a dipeptide of formula (XIII)

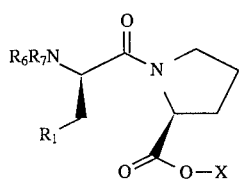 (XIII)

in which $R_1$ is as defined above, $R_6$ represents either a hydrogen atom when $R_7$ represents a straight or branched —$CO(C_1-C_4)$ alkyl group, or a straight or branched —$CO_2(C_1-C_4)$ alkyl group when $R_7$ represents a hydrogen atom, or a straight or branched $(C_1-C_4)$ alkyl group and X represents either the pyrrolidin-1-yl-2,5-dione group or the 2-methylpropyloxycarbonyl group.

10. A process for the synthesis of compounds of formula (1) according to claim 9 further comprising treating the compound of formula (1) with hydrochloric acid to obtain the corresponding salt.

\* \* \* \* \*